(12) United States Patent
Chen

(10) Patent No.: US 12,053,015 B2
(45) Date of Patent: Aug. 6, 2024

(54) AEROSOL-GENERATING ARTICLE, DEVICE, AND SYSTEM

(71) Applicant: SHENZHEN YUYAN INDUSTRIAL LIMITED, Shenzhen (CN)

(72) Inventor: Bin Chen, Shenzhen (CN)

(*) Notice: Subject to any disclaimer, the term of this patent is extended or adjusted under 35 U.S.C. 154(b) by 825 days.

(21) Appl. No.: 17/134,461

(22) Filed: Dec. 27, 2020

(65) Prior Publication Data

US 2021/0112852 A1    Apr. 22, 2021

Related U.S. Application Data

(63) Continuation of application No. PCT/CN2019/092847, filed on Jun. 25, 2019.

(30) Foreign Application Priority Data

Jun. 29, 2018 (CN) .......................... 201810697719.3

(51) Int. Cl.
| | |
|---|---|
| *A24F 40/465* | (2020.01) |
| *A24D 1/02* | (2006.01) |
| *A24D 1/20* | (2020.01) |
| *A24F 40/20* | (2020.01) |
| *A24F 40/53* | (2020.01) |
| *G06K 7/14* | (2006.01) |
| *G11B 5/78* | (2006.01) |
| *A61M 15/06* | (2006.01) |

(52) U.S. Cl.
CPC ............. *A24D 1/20* (2020.01); *A24D 1/02* (2013.01); *A24F 40/20* (2020.01); *A24F 40/465* (2020.01); *A24F 40/53* (2020.01); *G06K 7/1413* (2013.01); *G11B 5/78* (2013.01); *A61M 15/06* (2013.01)

(58) Field of Classification Search
None
See application file for complete search history.

(56) References Cited

U.S. PATENT DOCUMENTS

| | | | |
|---|---|---|---|
| 2014/0332019 A1 | 11/2014 | Liu | |
| 2016/0325858 A1* | 11/2016 | Ampolini | ............... B65B 59/001 |
| 2017/0196270 A1 | 7/2017 | Vick et al. | |
| 2017/0303593 A1* | 10/2017 | Cameron | ................ A24F 40/60 |

FOREIGN PATENT DOCUMENTS

| | | | | |
|---|---|---|---|---|
| CN | 203660013 | | 6/2014 | |
| CN | 105077592 A | | 11/2015 | |
| CN | 105111963 | | 12/2015 | |
| CN | 106604755 A | * | 4/2017 | ............. A24F 40/10 |
| CN | 106690422 | | 5/2017 | |

(Continued)

OTHER PUBLICATIONS

International Search Report of PCT/CN2019/092847.

(Continued)

*Primary Examiner* — Tho D Ta

(57) ABSTRACT

The present disclosure relates to an aerosol-generating article, including an article body and a magnetic recording medium disposed on a surface of the article body and/or inside the article body. The magnetic recording medium is an information storage unit storing readable information. The present disclosure also provides an aerosol-generating device and an aerosol-generating system.

20 Claims, 8 Drawing Sheets

(56) References Cited

FOREIGN PATENT DOCUMENTS

| | | | |
|---|---|---|---|
| CN | 2263068 | | 10/2018 |
| CN | 208850675 | | 5/2019 |
| JP | 2017515488 | A | 6/2017 |
| KR | 20180070511 | A * | 6/2018 |
| WO | WO2017036951 | | 3/2017 |
| WO | WO2017207442 | | 12/2018 |

OTHER PUBLICATIONS

OA1 for Japanese Application No. 2020-573185 dated Mar. 8, 2020 (7 pages).
Extended European Search Report for European Application No. 19826345.1 dated Sep. 24, 2021 (8 pages).

* cited by examiner

AEROSOL-GENERATING ARTICLE, DEVICE, AND SYSTEM

CROSS-REFERENCE TO RELATED APPLICATIONS

This application claims priority to China Patent Application No. 201810697719.3, filed on Jun. 29, 2018, entitled, "AEROSOL-GENERATING ARTICLE, DEVICE, AND SYSTEM", the content of which is hereby incorporated by reference in its entirety. This application is a continuation under 35 U.S.C. § 120 of international patent application PCT/CN2019/092847, filed on Jun. 25, 2019, the content of which is also hereby incorporated by reference in its entirety.

TECHNICAL FIELD

The present disclosure relates to an aerosol-generating article, an aerosol-generating device, and an aerosol-generating system.

BACKGROUND

Conventional electronic cigarettes or low-temperature heating cigarettes mainly rely on barcodes, such as one-dimensional codes or two-dimensional codes, for anti-counterfeiting identification and recording information such as the manufacturer, the production date, etc. The use of optical recognition systems to recognize barcodes is limited by various environmental factors, and the amount of information that a barcode can store is relatively small. In addition, the barcode usually needs to be printed on a flat surface to be recognized. The material and flatness of the printed surface have a great effect on barcode recognition.

SUMMARY

In view of this, there is a need to provide an aerosol-generating article, an aerosol-generating device, and an aerosol-generating system.

An aerosol-generating article includes an article body and a magnetic recording medium. The magnetic recording medium is disposed on a surface of the article body and/or inside the article body. The magnetic recording medium is an information storage unit storing readable information.

An aerosol-generating device configured to provide electrical or thermal energy to the aerosol-generating article. The aerosol-generating device is provided with an accommodating cavity configured to accommodate the aerosol-generating article. The aerosol-generating device includes an information read unit. The information read unit includes a magnetic head disposed in the accommodating cavity to read information.

An aerosol-generating system includes the aerosol-generating article and/or the aerosol-generating device.

In the embodiments of the present disclosure, the information storage unit is disposed in the aerosol-generating article, and the information read unit is disposed in the aerosol-generating device. When the aerosol-generating article is disposed in the accommodating cavity of the aerosol-generating device, the information stored in the information storage unit can be read by the aerosol-generating device. The information storage unit is a magnetic recording medium. The magnetic recording medium has a relatively large information storage capacity, can be disposed on surfaces with various shapes and materials by a more flexible manner, and has a broader application scope. Moreover, the magnetic recording medium is inexpensive, simple to arrange, and easy to implement.

DETAILED DESCRIPTION

Figure 1:
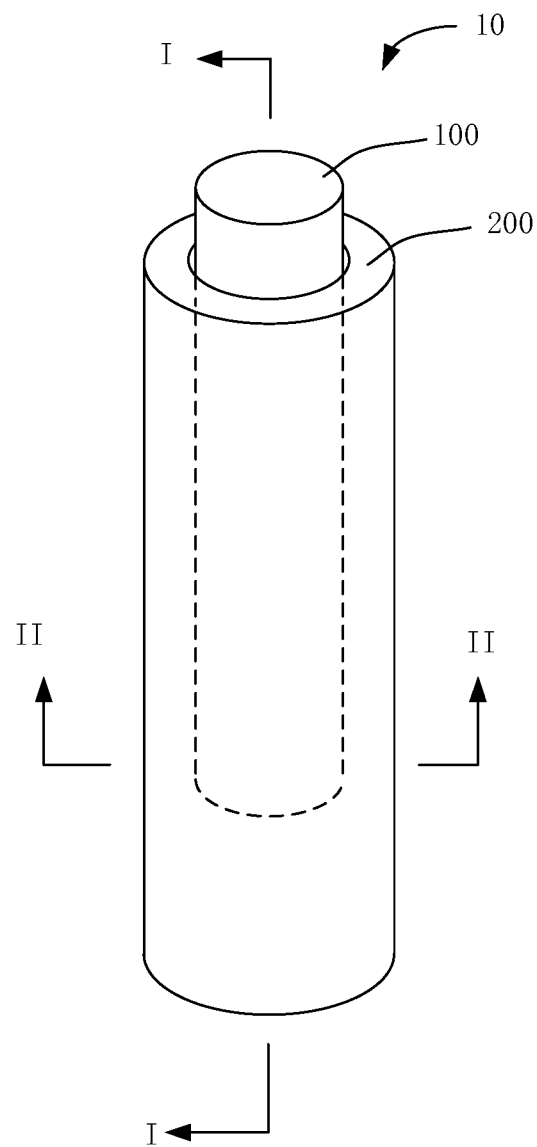
FIG. 1 is a schematic structural view of an aerosol-generating system provided by an embodiment of the present disclosure.

The present disclosure will now be described in detail with reference to the accompanying drawings and embodiments in order to make the objects, technical solutions, and advantages of the present disclosure more clear. It should be understood that the specific embodiments described herein are only for explaining the disclosure, and not intended to limit the present disclosure.

In the present disclosure, an element, when referred to as being "fixed" or "connected" to another element, may be directly fixed or connected to the other element or via an intermediate element. Rather when an element is referred to as being "directly" fixed or connected to another element, there is no intermediate element. The drawings are not necessarily drawn to scale, and various parts are drawn for better illustration of the embodiments.

In the embodiments of the present disclosure, the term "aerosol-generating article" refers to a product, e.g., a cigarette, a cartridge, or a smoking stick, containing a smoking material and being capable of generating an aerosol, e.g., smoke or mist, by heating. In an embodiment, the aerosol-generating article is a disposable product. The aerosol-generating article itself cannot provide electrical energy.

In the embodiments of the present disclosure, the term "aerosol-generating device" refers to a device, e.g., a smoking device, configured to provide electrical energy or thermal energy to an aerosol-generating article. The aerosol-generating device can directly provide thermal energy to heat the aerosol-generating article, or provide electrical energy to the aerosol-generating article, and the aerosol-generating article converts the electrical energy into thermal energy to heat the smoking material.

In the embodiments of the present disclosure, the term "smoking material" refers to a smoke-generating material, which is a material that can release flavor and/or nicotine and/or smoke when heated or burned, that is, a material that can be atomized, and that is, an aerosol-generating material. The smoking material can be in a solid, semi-solid, or liquid state. In considerations of air permeability, assembly, manufacture, etc., the solid smoking material is often processed into thin sheets, so is often called "sheets". Shredded sheets are also called smoking cuts. The smoking material mentioned in the embodiments of the present disclosure can be natural or synthetic smoking liquid, smoking oil, smoking glue, smoking paste, smoking cuts, tobacco leaves, etc. In an example, the synthetic smoking material contains glycerin, propylene glycol, nicotine, etc. The smoking liquid is in a liquid state, the smoking oil is oily, the smoking gel is gelatinous, and the smoking paste is creamy. The smoking cuts include natural, synthetic, or extracted and processed smoking cuts. The tobacco leaves include natural, synthetic, or extracted and processed tobacco leaves. The smoking material can be heated in the form of being sealed by other substances, such as stored in thermally degradable packaging, e.g., in microcapsules. After heated, prescribed volatile substances are released from the degraded or porous sealed packaging.

In the embodiments of the present disclosure, the smoking material may or may not contain nicotine. The smoking material containing nicotine can include at least one of smoking liquid, smoking oil, smoking glue, smoking paste, smoking cuts, tobacco leaves, and the like made from nicotine-containing materials and/or natural tobacco leaf products. The smoking liquid is in a liquid state, the smoking oil is oily, the smoking gel is gelatinous, and the smoking paste is creamy. The smoking cuts include natural, synthetic, or extracted and processed smoking cuts. The tobacco leaves include natural, synthetic, or extracted and processed tobacco leaves. The smoking material containing no nicotine mainly includes a flavor substance, such as a spice, which can be atomized to simulate the smoking process and assist to quit smoking. In an embodiment, the spice is peppermint oil. The smoking material can also include other additives, such as glycerin and/or propylene glycol.

In the embodiments of the present disclosure, the "readable information" includes but is not limited to at least one of the ingredients of the smoking material, the amounts of the ingredients of the smoking material, the most suitable heating method of the aerosol-generating article, the model, the serial number, the manufacturer, the distributor, the production date, the sale date, the expiration date, etc.

Referring to FIG. 1 to FIG. 5, an embodiment of the present disclosure provides an aerosol-generating system 10 including an aerosol-generating article 100 and an aerosol-generating device 200.

The aerosol-generating article 100 includes an article body 110 and a magnetic recording medium 160. The magnetic recording medium 160 is an information storage unit storing readable information. The magnetic recording medium 160 can be disposed on a surface of the article body 110 and/or inside the article body 110.

The article body 110 can include a smoking material 112 capable of generating aerosol. The magnetic recording medium 160 can cover the smoking material 112, be covered by the smoking material 112, and/or be disposed in the smoking material 112.

Figure 6:
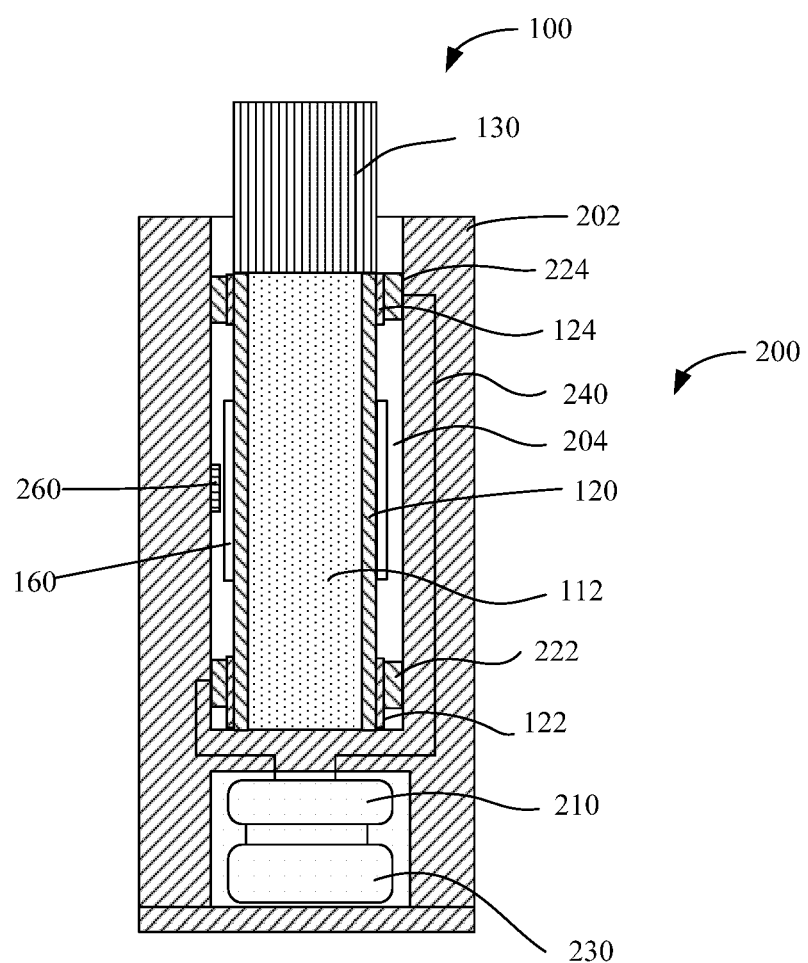
FIG. 6 is a schematic longitudinal sectional view of the aerosol-generating system provided by an embodiment of the present disclosure.

The article body 110 can further include a carrying tube 114 configured to enclose the smoking material 112. The carrying tube 114 can be made of, for example, a cigarette paper or an overwrap paper. The magnetic recording medium 160 can be disposed on an inner surface or an outer surface of the carrying tube 114. Referring to FIG. 6, the aerosol-generating device 200 is provided with an accommodating cavity 204 configured to accommodate the aerosol-generating article 100. The aerosol-generating device 200 includes an information read unit. The information read unit includes a magnetic head 260 disposed in the accommodating cavity 204 and configured to read the readable information.

In the embodiments of the present disclosure, the information storage unit is disposed in the aerosol-generating article 100, and the information read unit is disposed in the aerosol-generating device 200. When the aerosol-generating article 100 is disposed in the accommodating cavity 204 of the aerosol-generating device 200, the information stored in the information storage unit can be read by the aerosol-generating device 200. The information storage unit is the magnetic recording medium 160. The magnetic recording medium 160 has a relatively large information storage capacity, can be disposed on surfaces with various shapes and materials by a more flexible manner, and has a broader application scope. Moreover, the magnetic recording medium 160 is inexpensive, simple to arrange, and easy to implement.

In an embodiment, the read information is transmitted to a display screen located on a housing of the aerosol-generating device 200. The user can identify an authenticity of the aerosol-generating article 100 according to the read information, or can adjust a method for using the aerosol-generating article 100 according to the read information. It can be understood that the information stored in the information storage unit is not limited to be read by using the information read unit located in the aerosol-generating device 200. Other information reading devices can also be used to read the information stored in the information storage unit.

In an embodiment, the readable information is attenuated or disappears at a temperature greater than a preset temperature; or the magnetic recording medium 160 is weakened in magnetic strength or demagnetizes at a temperature greater than the preset temperature. For example, the spontaneous magnetization of the magnetic recording medium 160 decreases when the temperature is higher than the preset temperature. The higher the temperature, the weaker the spontaneous magnetization, which may even disappear directly. The preset temperature can be in a range from 100°

C. to 300° C. When the aerosol-generating article 100 has been smoked, the stored information thereof is attenuated to be unreadable or even disappears. This ensures that every aerosol-generating article 100 whose information is readable is an aerosol-generating article that has not ever been heated. The readable information can be erased easily and effectively without the need of other particular treatments.

In some embodiments, the magnetic recording medium 160 can be a quasi two-dimensional structure, such as a sheet, a layer, or a film. The magnetic recording medium 160 can be rigid or flexible, and for example, can have a certain strength, but can be bent. The quasi two-dimensional magnetic recording medium 160 can be further bent or rolled up, so that the aerosol-generating article 100 with a constant volume can accommodate a magnetic recording medium 160 with a larger area.

The magnetic recording medium 160 can include a magnetic recording material layer 161. The magnetic recording material refers to a type of material that uses rectangular hysteresis loops or magnetic moment changes to store information. The magnetic recording material can be a material in the form of particles (i.e., magnetic powder) or a continuous film shaped material.

The magnetic recording medium 160 can further include a substrate 162. The substrate 162 supports the magnetic recording material layer 161 and can be a layer shaped substrate. The magnetic recording material layer 161 can be stacked on a surface of the substrate 162. The material of the substrate 162 can be a non-magnetic material, for example, a polymer layer or a non-magnetic metal layer.

On the condition that the magnetic recording material is in the form of particles, the magnetic recording material particles can be uniformly distributed on the surface of the substrate 162 to form the magnetic recording material layer 161. For example, a magnetic slurry made of the magnetic recording material particles, a non-magnetic adhesive, and solvent is coated on the surface of the substrate 162 to form the magnetic recording material layer 161. The magnetic recording material in the particle form can be at least one of magnetic metal oxide powder and magnetic metal powder. The magnetic metal oxide powder includes but is not limited to at least one of magnetic $\gamma$-$Fe_2O_3$ powder, magnetic $Fe_3O_4$ powder, and magnetic $CrO_2$ powder. The magnetic metal powder includes but is not limited to at least one of magnetic Fe powder, magnetic Co powder, magnetic Ni powder, magnetic Fe-based alloy powder, magnetic Co-based alloy powder, and magnetic Ni-based alloy powder. In an example, the magnetic recording material particles can be in the shape of needles.

On the condition that the magnetic recording material is a continuous film shaped material, the magnetic recording material layer 161 can be made of a continuous magnetic recording material. For example, the magnetic recording material layer 161 can be a Co-based alloy layer. The Co-based alloy can be, for example, a Co—Ni—P alloy, a Fe—Ni—Co alloy, a Co—P alloy, etc. The magnetic recording material layer 161 can have a multilayer film structure. For example, the magnetic recording material layer can be made of two magnetic metal layers and a non-magnetic metal layer sandwiched between the two magnetic metal layers. A magnetic decoupling between the two magnetic metal layers can be induced by the non-magnetic metal layer, so that the two magnetic metal layers can gain high coercivity. The magnetic recording material layer 161 can be formed on the substrate 162 by electroplating, chemical plating, sputtering, evaporation, or ion plating.

The readable information can be in an encoded form and recorded in the magnetic recording material layer 161. Specifically, binary digital information can be converted into magnetization reversal of a magnetic recording material and recorded in the magnetic recording material layer 161. For example, in order to record "1", the magnetic recording material transitions from an unmagnetized state to a saturation magnetization state in the first direction; in order to record "0", the magnetic recording material transitions from the unmagnetized state to the saturation magnetization state in the second direction. A recording track of the information forms a magnetic track. The readable information can be stored along the magnetic track in the magnetic recording material layer 161.

Figure 2:
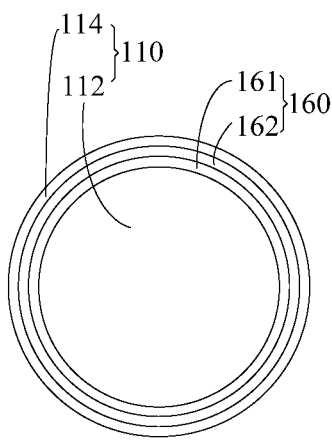
FIG. 2 is a schematic cross-sectional view of an aerosol-generating article having an information storage unit provided by an embodiment of the present disclosure.
Figure 3:
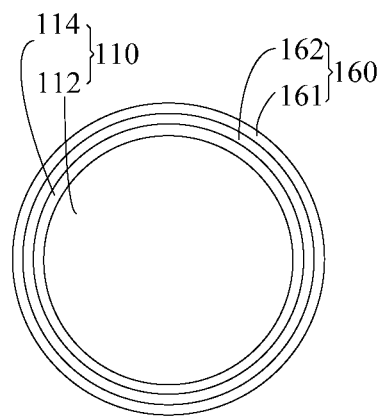
FIG. 3 is a schematic cross-sectional view of the aerosol-generating article having the information storage unit provided by another embodiment of the present disclosure.

Referring to FIG. 2 and FIG. 3, in some embodiments, the entire smoking material 112 as a whole can be enclosed by the quasi two-dimensional magnetic recording medium 160. For example, the entire smoking material 112 as a whole is formed into a rod or a stick. The magnetic recording medium 160 is bent into a tubular structure and is sleeved around the periphery of the entire smoking material 112. In an embodiment, the magnetic recording medium 160 also functions as a carrying tube, not only recording information but also wrapping, supporting, and accommodating the smoking material 112, so that there is no need to additionally provide the carrying tube 114.

In another embodiment, the article body 110 can also separately include the carrying tube 114 that encloses the entire smoking material 112. In an embodiment, the carrying tube 114 is stacked with the magnetic recording medium 160. Referring to FIG. 2, in an embodiment, the periphery of the magnetic recording medium 160 can be wrapped by the carrying tube 114. Referring to FIG. 3, in another embodiment, the carrying tube 114 can be sandwiched between the magnetic recording medium 160 and the smoking material 112. In these two embodiments, the carrying tube 114 is made of a non-magnetic material.

Figure 4:
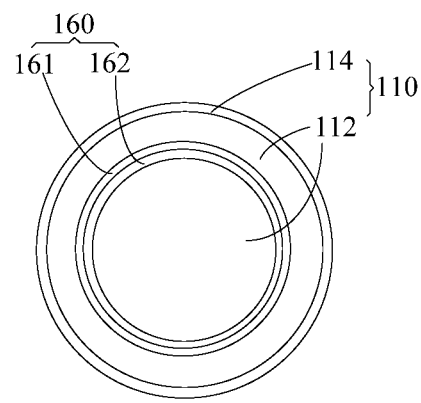
FIG. 4 is a schematic cross-sectional view of the aerosol-generating article having the information storage unit provided by yet another embodiment of the present disclosure.

In another embodiment, as shown in FIG. 4, the magnetic recording medium 160 with the tubular structure is embedded in the smoking material 112. A portion of the smoking material 112 is disposed in the tubular structure of the magnetic recording medium 160, and another portion of the smoking material 112 is disposed outside the magnetic recording medium 160 and wraps an outer surface of the magnetic recording medium 160. The tubular magnetic recording medium 160 and the carrying tube 114 can be concentrically arranged and spaced apart from each other. Of course, the tubular structure of the magnetic recording medium 160 can be filled with no smoking material 112. For example, another element, such as a support rod, can be placed inside the tubular structure of the magnetic recording medium.

Figure 5:
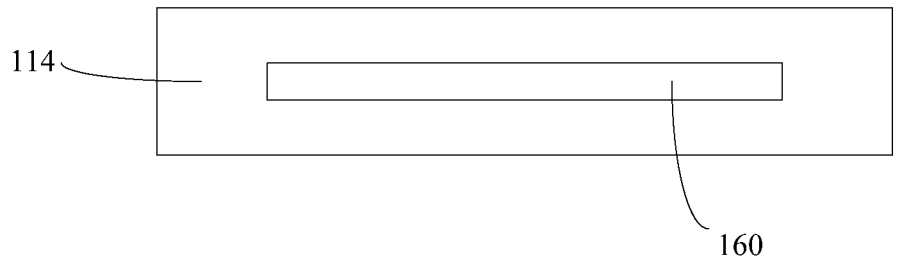
FIG. 5 is a schematic front view of the aerosol-generating article having the information storage unit provided by another embodiment of the present disclosure.

Referring to FIG. 5. In some other embodiments, the quasi two-dimensional magnetic recording medium 160 can be strip-shaped. The entire smoking material 110 as a whole can be enclosed by the carrying tube 114. The strip-shaped magnetic recording medium 160 can be disposed on the surface (i.e., the inner surface or the outer surface) of the carrying tube 114, and the surface can be adjacent to or away from the smoking material 112. The strip-shaped magnetic recording medium 160 can extend along an axial direction of the article body 110. In some other embodiments, the strip-shaped magnetic recording medium 160 can be disposed in the smoking material 112 and wrapped by the smoking material 112.

In the embodiments that the magnetic recording medium 160 is disposed on the surface (i.e., the inner surface or the outer surface) of the carrying tube 114, and the surface is adjacent to or away from the smoking material 112, the magnetic recording material layer 161 can be directly disposed on the inner surface or the outer surface of the carrying tube 114. For example, the magnetic slurry can be coated on the inner surface or the outer surface of the carrying tube 114, or the magnetic recording material layer 161, such as an alloy layer, can be directly plated or deposited on the inner surface or the outer surface of the carrying tube 114. On this condition, the carrying tube 114 can also functions as the substrate 162. Of course, the magnetic recording material layer 161 can also be bonded to the inner surface or the outer surface of the carrying tube 114 through the substrate 162. For example, the surface of the substrate 162 away from the magnetic recording material layer 161 can be bonded to the inner surface or the outer surface of the carrying tube 114.

In an embodiment, the magnetic recording medium 160 is disposed on the outer surface of the carrying tube 114. When the magnetic head 260 reads the information stored in the magnetic recording medium 160, a distance from the magnetic head 260 to the magnetic recording medium 160 is smaller, which is more conducive to information reading. In an embodiment, in arrangement of the magnetic recording medium 160, a distance between the substrate 162 and an axis of the aerosol-generating article 100 is smaller than a distance between the magnetic recording material layer 161 and the axis of the aerosol-generating article 100, so that the magnetic head 260 can be closer to the magnetic recording material layer 161 when reading the information stored in the magnetic recording medium 160, which is more conducive to information reading. In an embodiment, the magnetic recording material layer 161 is directly disposed on the carrying tube 114, that is, the carrying tube 114 can be a substrate for supporting the magnetic recording material layer 161. This arrangement is simpler, which not only saves raw materials, but also simplifies the preparation process of the aerosol-generating article 100.

Referring to FIG. 6, the information read unit of the aerosol-generating device 200 can include a magnetic head 260 configured to read information. The aerosol-generating device 200 can include a housing. The housing can be provided with the accommodating cavity 204 configured to accommodate the aerosol-generating article 100. The magnetic head 260 can be disposed in the accommodating cavity 204. Moreover, the position of the magnetic head 260 exactly faces the magnetic track of the magnetic recording medium 160 when the aerosol-generating article 100 is inserted into the accommodating cavity 204. The magnetic head 260 can be spaced from the magnetic recording medium 160, as long as the distance between the magnetic head 260 and the magnetic recording medium 160 is within an effective sensing range of the magnetic head 260.

A main function of the magnetic head 260 is to realize electromagnetic energy conversion. In an embodiment, the magnetic head 260 includes a toroidal core with a narrow gap and a coil wound around the toroidal core. The magnetic recording medium 160 can affect the magnetic field at the narrow gap defined by the magnetic head, thereby inducing a current change in the coil. The readable information in the magnetic recording medium 160 is thereby converted into electrical signal output. The material of the core can be a soft magnetic material with a high magnetic permeability. The material of the core can be, for example, one or more selected from alloy magnetic core materials, ferrite magnetic core materials, amorphous magnetic core materials, and microcrystalline thin-film magnetic core materials. The alloy magnetic core materials can be, for example, molybdenum permalloy materials or Sendust magnetic core materials.

Figure 7:
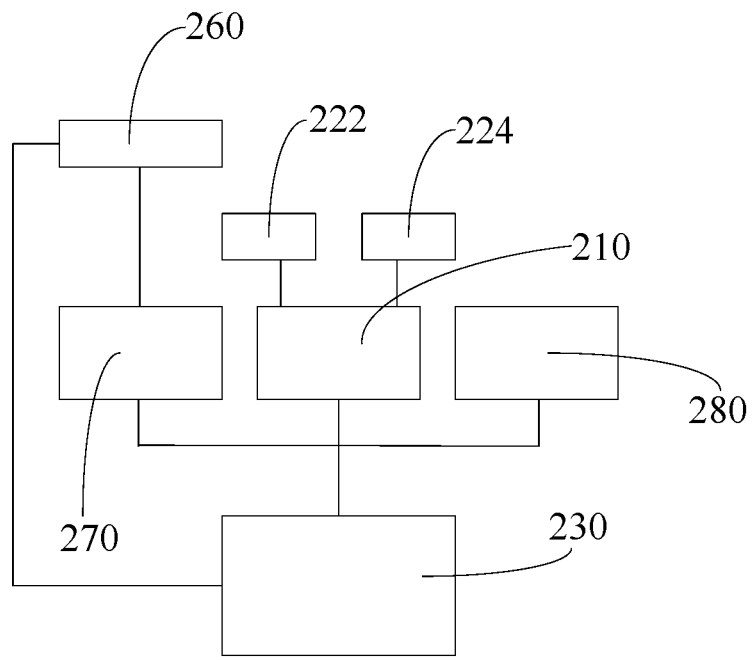
FIG. 7 is a schematic block diagram showing a connection in units of an aerosol-generating device provided by an embodiment of the present disclosure.

Referring to FIG. 7, in an embodiment, the aerosol-generating device 200 further includes a drive unit configured to drive the magnetic head 260 and/or the aerosol-generating article 100 to move relative to each other. For example, the aerosol-generating device 200 further includes a magnetic head drive unit 270 configured to drive the magnetic head 260 to move relative to the magnetic recording medium 160, thereby reading the readable information stored in the magnetic recording medium 160. When the magnetic recording medium 160 is a tubular structure, the magnetic head 260 driven by the magnetic head drive unit 270 can rotate around the circumference of the aerosol-generating article 100 to read information. When the magnetic recording medium 160 is a strip-shaped structure extending along the axial direction of the aerosol-generating article 100, the magnetic head 260 driven by the magnetic head drive unit 270 can move along the axial direction of the aerosol-generating article 100 to read information. The magnetic head drive unit 270 can include a drive device and a transmission device. The magnetic head 260 can be connected to the drive device through the transmission device. The transmission device can include at least one of a slider-crank mechanism, an oscillating guide bar mechanism, an eccentric wheel mechanism, a hinged bar mechanism, a rack-and-pinion assembly, etc.

Of course, in the embodiment that the drive unit drives the aerosol-generating article 100 to move relative to the magnetic head 260, the drive unit can alternatively be an aerosol-generating article drive unit. The aerosol-generating article drive unit is connected to the aerosol-generating article 100 and drives the aerosol-generating article 100 to circumferentially rotate along the accommodating cavity 204 or drives the aerosol-generating article 100 to move along the axial direction of the accommodating cavity 204. The movement of the aerosol-generating article 100 causes the magnetic head 260 to circumferentially rotate or axially move relative to the aerosol-generating article 100 to read information.

In an embodiment, the aerosol-generating device 200 further includes a control unit 230. The control unit 230 can be electrically connected to the magnetic head 260 and is configured to receive the information obtained by the magnetic head 260. The aerosol-generating device 200 can further include a display unit 280. The control unit 230 can transmit the information obtained by the magnetic head 260 to the display unit 280 to display. The control unit 230 can be further connected to the magnetic head drive unit 270 to control a moving path of the magnetic head 260. The magnetic head drive unit 270, the control unit 230, and the display unit 280 can be arranged on the housing.

In an embodiment, a plurality of magnetic heads 260 can be arranged at different positions in the accommodating cavity 204. On the condition that the magnetic recording medium 160 is a tubular structure, the plurality of magnetic heads 260 can be arranged along the circumferential direction of the accommodating cavity 204. On the condition that the magnetic recording medium 160 is a strip-shaped structure extending along the axial direction of the aerosol-generating article 100, the plurality of magnetic heads 260 can be arranged along the axial direction of the accommodating cavity 204. A magnetic head 260 that is closest to the magnetic recording medium 160 in the plurality of magnetic heads 260 can be used to read the information, in case the aerosol-generating article 100 is not installed in the accommodating cavity 204 according to a preset manner, preventing the magnetic recording medium 160 from not corresponding to the magnetic head 260. A plurality of tracks corresponding to the plurality of magnetic heads 260 can be disposed in the magnetic recording medium 160, or a plurality of magnetic recording mediums 160 corresponding to the plurality of magnetic heads 260 can be disposed on the aerosol-generating article 100. The plurality of magnetic recording mediums 160 can store the same or different readable information.

Referring to FIG. 6, an embodiment of the aerosol-generating article 100 provided by the present disclosure can further include an electric heating member 120 disposed adjacent to the smoking material 112 and capable of heating the smoking material 112. The electric heating member 120 is a member that converts electrical energy into thermal energy. The electric heating member 120 can cover the smoking material 112, be covered by the smoking material 112, and/or be disposed in the smoking material 112. By disposing the electric heating member 120 in the article body 110, that is, having the electric heating member 120 as a part of the aerosol-generating article 100, the smoking material 112 and the electric heating member 120 can realize better and sufficient contact with each other during the manufacture of the aerosol-generating article 100, thereby improving heating efficiency. The electric heating member 120 can have varied shapes and structures and does not need to have a high mechanical strength to withstand the pressure in repeatedly inserting into smoking materials 112.

The aerosol-generating article 100 can be a disposable product, so that the electric heating member 120 can also be disposable, which avoids the problems caused by repetitive use of the same electric heating member 120, for example, the problems of contamination and harmful substance accumulation caused by tar and other substances which are remained on the surface of the electric heating member 120 and difficult to be removed. In an embodiment, the aerosol-generating article 100 is a disposable cigarette.

In an embodiment, the electric heating member 120 is a quasi two-dimensional structure, such as a sheet, a layer, or a film, thereby having a relatively large surface area. The quasi two-dimensional electric heating member 120 can be rigid or flexible, for example, can have certain strength, but can be bent. The quasi two-dimensional electric heating member 120 can be further bent or rolled up, so that the aerosol-generating article 100 with a constant volume can accommodate an electric heating member 120 with a larger area. A thickness of the quasi two-dimensional electric heating member 120 can be ranged from 1 nanometer to 1 millimeter, in an embodiment, can be ranged from 500 nanometers to 500 micrometers, and in another embodiment, can be ranged from 1 micrometer to 130 micrometers.

The electric heating member 120 can be made of one or more materials selected from, but not limited to, carbon nanotubes, carbon nanotube films, graphene, carbon fibers, carbon fiber films, carbon films, carbon fiber textiles, and metals, alloys, and metal compounds, such as gold, silver, copper, aluminum, nickel, chromium, iron, stainless steel, nickel-chromium alloys, metal oxides, iron-chromium-aluminum alloys, palladium alloys, and amorphous metal alloys, which generates heat by conducting electricity, and other derivatives and compounds with carbon as a constituent element.

In some other embodiments, the material of the electric heating member 120 can be a solid composite material obtained by compositing two or more materials with different physical and chemical properties, one of which can be an electrical conducting material, such as metal, semiconductor, conductive polymer, or carbon material, and another of which can be selected from, but not limited to, resin, rubber, ceramic, fiber, synthetic polymer. For example, the composite material can be silicon rubber, a composite of rubber and conductive polymer, a composite of carbon fibers and graphene, a composite of conductive polymer and ceramics, a carbon fiber paper (composited from chopped carbon fibers, pulp, and other polymer additives), a carbon paper (composited from carbon powder or graphite powder, pulp, and other additives), a polyimide heating film, etc. The polyimide heating film is also known as a polyimide film.

Figures 8, 9:
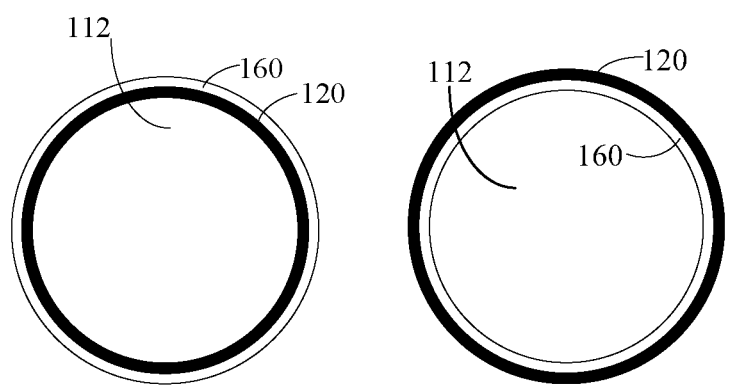
FIG. 8 is a schematic cross-sectional view of the aerosol-generating article having the information storage unit and an electric heating member provided by an embodiment of the present disclosure.
FIG. 9 is a schematic cross-sectional view of the aerosol-generating article having the information storage unit and the electric heating member provided by another embodiment of the present disclosure.

Referring to FIG. 8 and FIG. 9, in an embodiment, the periphery of the entire smoking material 110 as a whole can be wrapped by the quasi two-dimensional electric heating member 120 which forms a tubular structure. The electric heating member 120 itself can also function as an overwrap paper or a carrying tube, not only electrically heating the smoking material 112 but also overall wrapping, supporting, and accommodating the smoking material 112. Of course, the aerosol-generating device 200 can additionally include the carrying tube 114. The periphery of the electric heating member 120 can be wrapped by the carrying tube 114, or the carrying tube 114 can be sandwiched between the electric heating member 120 and the smoking material 112. In the latter embodiment, the carrying tube 114 has a relatively good thermal conductivity.

In another embodiment, the quasi two-dimensional electric heating member 120 can be in a spiral shape and disposed in the smoking material 112. For example, the aerosol-generating article 100 can be manufactured by a method similar to that for traditional cigarettes. That is, the smoking material 112 is firstly formed into a smoking material sheet, and the quasi two-dimensional electric heating member 120 is stacked on the smoking material sheet to form a laminated structure. Then, the laminated structure is rolled up to form a rod or a stick to obtain the spiral-shaped electric heating member 120 disposed in the smoking material 112.

It can be understood that the electric heating member 120 is not limited to the quasi two-dimensional structure. For example, the electric heating member 120 can include one or more quasi one-dimensional structures, such as heating rods, heating sticks, or heating wires.

In an embodiment, the electric heating member 120 includes an electric heating material uniformly mixed with the smoking material 112. The electric heating material is in shape of, for example, powder, flakes, small particles, or short fibers. The electric heating material and the smoking material 112 are mixed together and connected to each other to form an electrical conducting path, so that the electric current is more uniformly conducted to the inner portion of the aerosol-generating article 100, to uniformly heat local regions of the smoking material 110. A size of the electric heating material can be, for example, 10 nanometers to 5 millimeters. The electric heating material can be, for example, metal or alloy in shape of powder or shreds, or conductive carbon materials, such as carbon nanotubes, graphene sheets, carbon fibers, amorphous carbon, or graphite particles or powder.

The positional relationship between the magnetic recording medium 160 and the electric heating member 120 can be varied in different embodiments. For example, the magnetic recording medium 160 and the electric heating member 120 can be stacked with or spaced from each other. The magnetic recording medium 160 and the electric heating member 120 can be, or can be not, in contact with each other.

On the condition that the magnetic recording medium 160 is stacked on the electric heating member 120, the magnetic recording medium 160 can be attached to the surface of the tubular shaped electric heating member 120. For example, the surface, away from the magnetic recording material layer 161, of substrate 162 of the magnetic recording medium 160 can be attached to the surface of the tubular shaped electric heating member 120 through an adhesive or the like. The magnetic recording material layer 161 can also be formed on the surface of the electric heating member 120 by coating, plating or spraying, so as to directly form the magnetic recording medium 160. That is, the electric heating member 120 can function as the substrate of the magnetic recording medium 160.

Figures 10, 11:
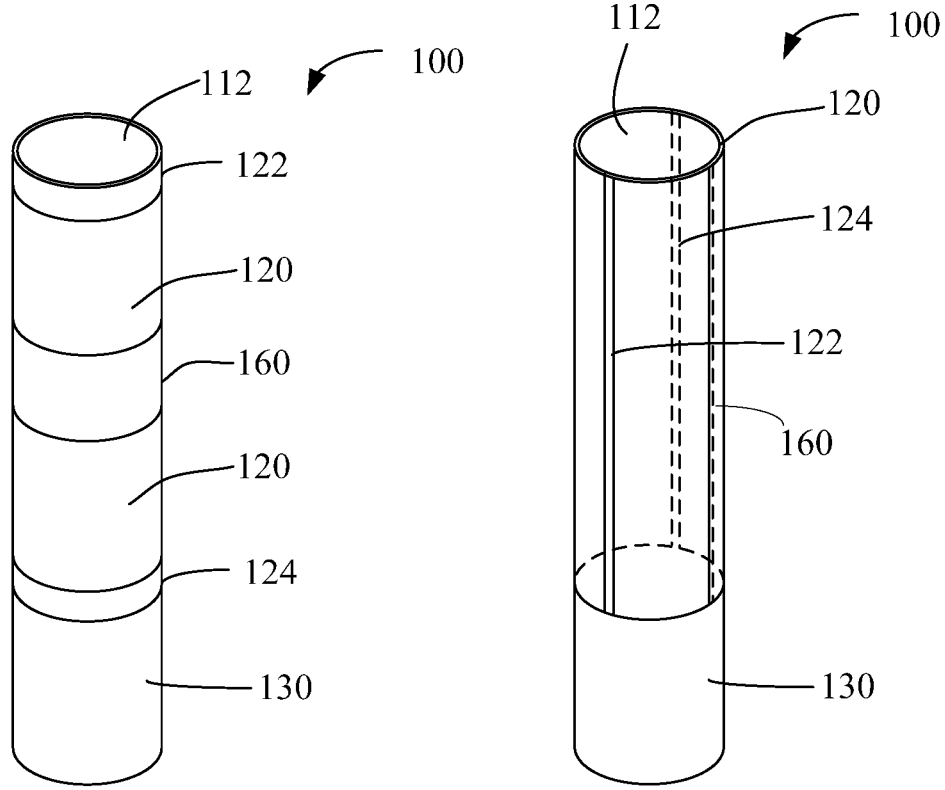
FIG. 10 is a schematic structural view of the aerosol-generating article having a first article-electrode and a second article-electrode according to an embodiment of the present disclosure.
FIG. 11 is a schematic structural view of the aerosol-generating article having the first article-electrode and the second article-electrode according to another embodiment of the present disclosure.

Referring to FIG. 8 and FIG. 10, in an embodiment, the magnetic recording medium 160 and the electric heating member 120 are both tubular structures, and the magnetic recording medium 160 is stacked on the outer surface of the tubular shaped electric heating member 120. Referring to FIG. 9, in another embodiment, the magnetic recording medium 160 and the electric heating member 120 are both tubular structures, and the magnetic recording medium 160 is stacked on the inner surface of the tubular shaped electric heating member 120. On the condition that the magnetic recording medium 160 is stacked on the outer surface of the tubular shaped electric heating member 120, the magnetic head 260 can be closer to the magnetic recording medium 160 when reading the information, which is more conducive to information reading.

Referring to FIG. 11, in another embodiment, the magnetic recording medium 160 can be a strip-shaped structure, the electric heating member 120 can be a tubular structure, and the strip-shaped magnetic recording medium 160 can be disposed on the inner surface or the outer surface of the electric heating member 120 and extend along the axial direction of the aerosol-generating article 100. On the condition that the strip-shaped magnetic recording medium 160 is stacked on the outer surface of the tubular shaped electric heating member 120, the magnetic head 260 can be closer to the magnetic recording medium 160 when reading the information, which is more conducive to information reading.

Since the magnetic recording medium 160 is directly disposed on the surface of the electric heating member 120, when the user puffs on the aerosol-generating article 100, the magnetic recording medium 160 will gradually demagnetize as the electric heating member 120 heats up, to remove the readable information. In this way, once the information can be read, it can be ensured that it is the first time the aerosol-generating article 100 has ever been used.

The magnetic recording medium 160 and electric heating member 120 stacked in the above-described two ways can function as the carrying tube 114 of the aerosol-generating article 100, so that there is no need to additionally provide the carrying tube 114.

In another embodiment, the tubular shaped electric heating member 120 can also function as the carrying tube of the aerosol-generating article 100, and the tubular shaped or strip-shaped magnetic recording medium 160 can be disposed in a cavity defined by the electric heating member 120 and wrapped by the smoking material 112. The electric heating member 120 and the magnetic recording medium 160 can be spaced from each other.

In an embodiment, the electric heating member 120 can be made of a material with both electric heating effect and magnetic property, or a mixture of an electric heating material and a magnetic material, so that the electric heating member 120 can simultaneously function as the magnetic recording medium 160, simplifying the preparation of the aerosol-generating article 100. The material that has both electric heating effect and magnetic property can be, for example, a Co-based alloy layer. The Co-based alloy can be, for example, a Co—Ni—P alloy, a Fe—Ni—Co alloy, a Co—P alloy, etc. It should be understood that when the electric heating member 120 and the magnetic recording medium 160 are two independent members, the electric heating member 120 is made of a non-magnetic material to prevent the electric heating member 120 from shielding or affecting the induction of magnetic head 260 on the magnetic recording medium 160.

The aerosol-generating device 200 further includes device-electrodes disposed in the accommodating cavity 204, for supplying electric power to the electric heating member 120. The device-electrodes can be, for example, a first device-electrode 222 and a second device-electrode 224. Theoretically, as long as the two ends of the electric heating member 120 are respectively connected to the device-electrodes of the aerosol-generating device 200, the electric power can be supplied to the electric heating member 120 to electric heat the adjacent smoking material 110. For example, when the electric heating member 120 is the tubular structure and wraps the smoking material 112, parts of the electric heating member 120 facing the device-electrodes can be in direct contact with the device-electrodes to achieve the electrical connection. To be better electrically connected to the device-electrodes, the aerosol-generating article 100 can include article-electrodes, such as a first article-electrode 122 and a second article-electrode 124. A material of the article-electrodes can have greater conductivity than that of the electric heating member 120. The article-electrodes can be in shape of a layer, a film, a wire, a sheet, or a block. The article-electrodes can be respectively welded to the electric heating member 120, fixedly connected to the electric heating member 120 by snap-fit structures, or bonded to the electric heating member 120 by conductive glue. Otherwise, the article-electrodes can be formed on the surface of the electric heating member 120 through film plating, spray coating, or printing.

In order to easily cause the device-electrodes of the aerosol-generating device 200 and the article-electrodes of the aerosol-generating article 100 to be in contact with each other to achieve the electrical connection, the locations of the device-electrodes in the accommodating cavity 204 and the locations of the article-electrodes on the aerosol-generating article 100 are corresponded to each other, so that the device-electrodes directly face the article-electrodes when the aerosol-generating article 100 is disposed in the aerosol-generating device 200. In an embodiment, the size (e.g., the radial size) of the aerosol-generating article 100 matches the size (e.g., the radial size) of the accommodating cavity 204, so that the device-electrodes and the article-electrodes can be in contact with each other at the beginning of the use.

Referring to FIG. 6 and FIG. 10, in an embodiment, the aerosol-generating article 100 is a column structure, and the first article-electrode 122 and the second article-electrode 124 are annular structures disposed around the circumference of the column structure. The electric heating member 120 is a tubular structure. The first article-electrode 122 and the second article-electrode 124 are respectively disposed at two ends of the tubular structure in the axial direction and extend circumferentially around the aerosol-generating article 100, so that every location of the electric heating member 120 is evenly supplied with the electric current to make the temperature uniform. Correspondingly, the housing of the aerosol-generating device 200 includes a tubular sidewall 202 defining the accommodating cavity 204, and the device-electrodes include an annular-shaped first device-electrode 222 and an annular-shaped second device-electrode 224, which are circumferentially disposed on the inner surface of the tubular sidewall 202. The locations of the first device-electrode 222 and the second device-electrode 224 in the axial direction of the accommodating cavity 204 respectively correspond to the locations of the first article-electrode 122 and the second article-electrode 124, so that the first device-electrode 222 directly faces the first article-electrode 122, and the second device-electrode 224 directly faces the second article-electrode 124, when the aerosol-generating article 100 is disposed in the aerosol-generating device 200. The outer diameters of the annular-shaped first article-electrode 122 and the annular-shaped second article-electrode 124 are equal to or slightly smaller than the inner diameters of the annular-shaped first device-electrode 222 and the annular-shaped second device-electrode 224.

In this embodiment, the magnetic recording medium 160 also can be an annular structure or a tubular structure, and extend along the circumference of the aerosol-generating article 100. The magnetic head 260 can rotate around the circumference of the aerosol-generating article 100 when reading information. The magnetic head 260 is prevented from approaching the article-electrodes and/or the device-electrodes during the rotation. During the user puffs on the aerosol-generating article 100, the temperature about the electrodes is relatively high, which may damage the magnetic head 260. In an embodiment, the magnetic recording medium 160 can be disposed at a middle portion between the first article-electrode 122 and the second article-electrode 124 and spaced from the first article-electrode 122 and the second article-electrode 124.

Figure 12:
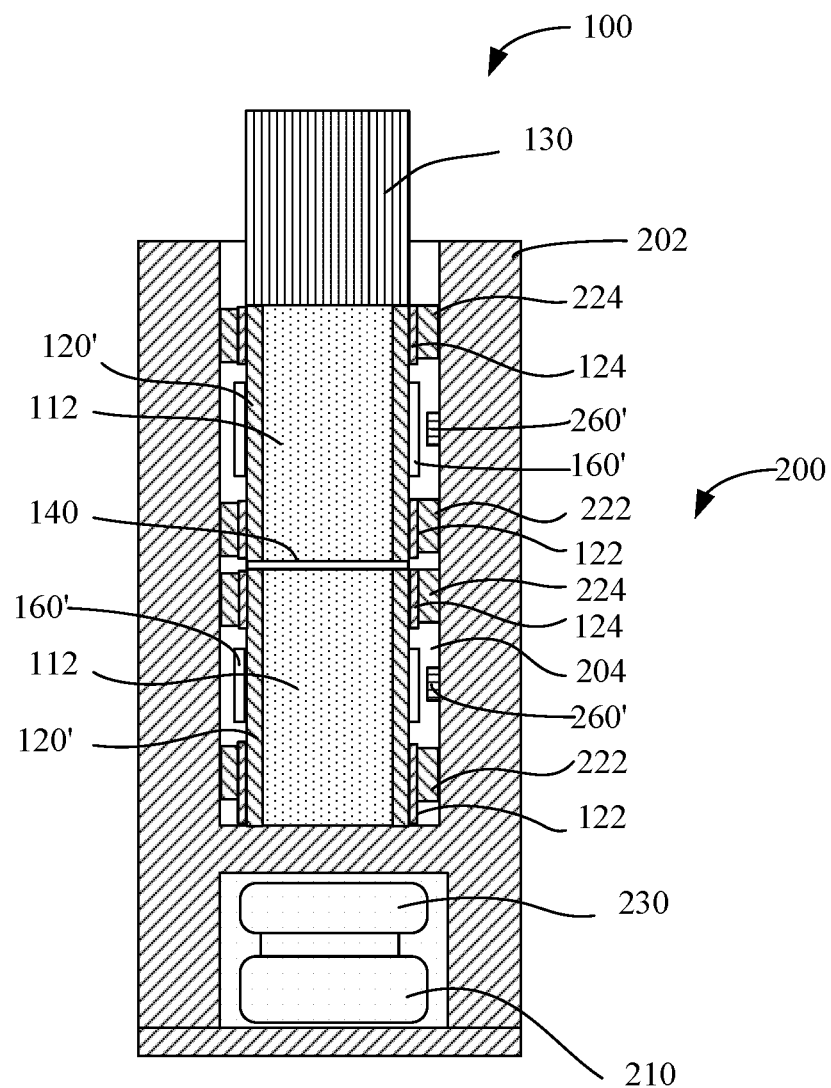
FIG. 12 is a schematic longitudinal sectional view of the aerosol-generating system provided by another embodiment of the present disclosure.
Figure 13:
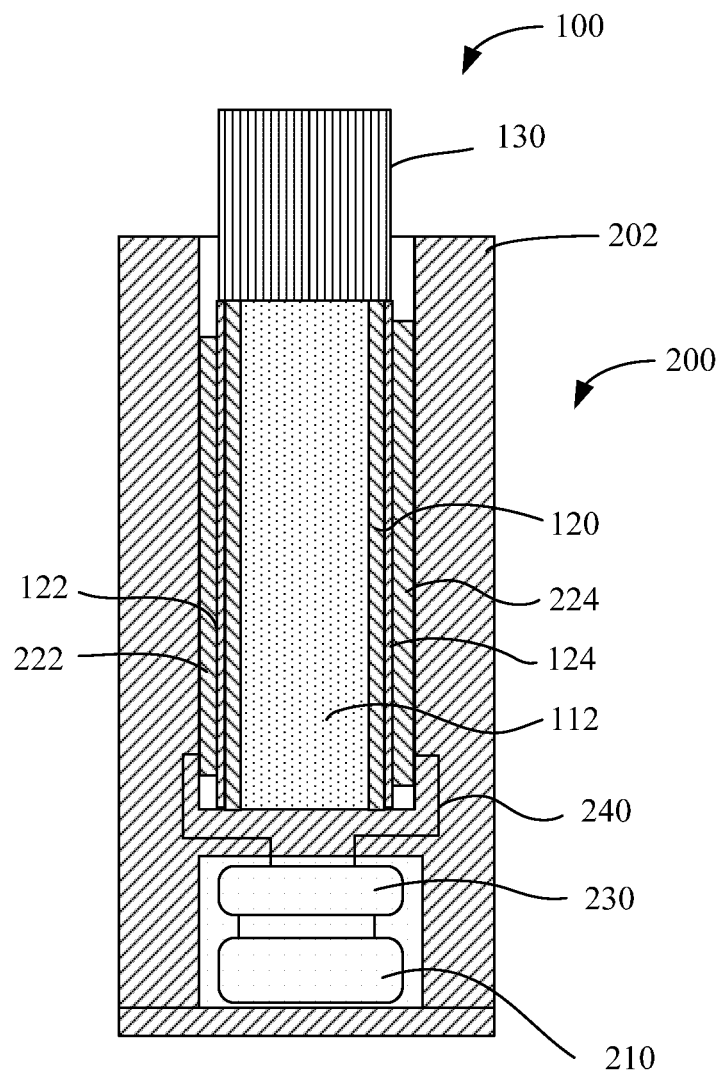
FIG. 13 is a schematic longitudinal sectional view of the aerosol-generating system provided by yet another embodiment of the present disclosure.
Figure 14:
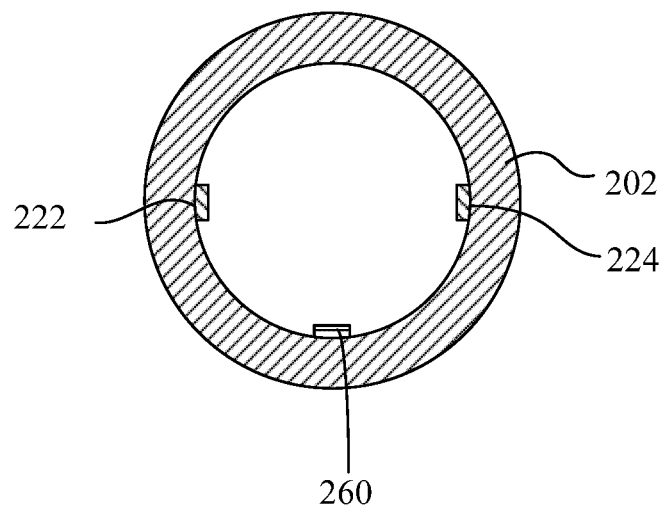
FIG. 14 is a schematic cross-sectional view of the aerosol-generating device in FIG. 13.
Figure 15:
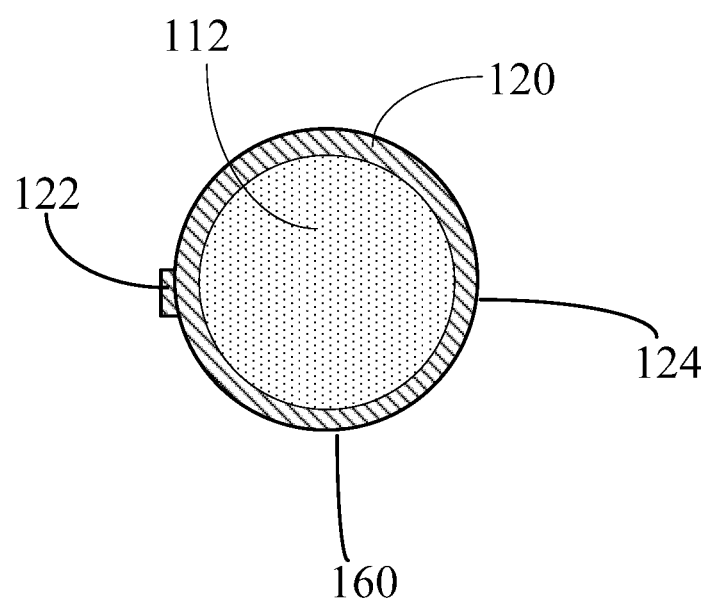
FIG. 15 is a schematic cross-sectional view of the aerosol-generating article in FIG. 13.

Referring to FIG. 12, in another embodiment, the aerosol-generating article 100 further includes a thermal insulating layer 140 configured to separate the smoking material 112 into different regions. The article-electrodes of the aerosol-generating article 100 include a plurality of article-electrode pairs each including a first article-electrode 122 and a second article-electrode 124. The electric heating member 120 also includes a plurality of sub-heating-elements 120', and each sub-heating-element 120' is connected to one article-electrode pair, configured to heat the different regions of the smoking material 112. That is, all regions include their respective sub-heating-elements 120' and article-electrode pairs. Correspondingly, the device-electrodes include a plurality of device-electrode pairs each including a first device-electrode 222 and a second device-electrode 224. The plurality of device-electrode pairs are disposed at different positions and can be independently controlled. The positions of the plurality of article-electrode pairs correspond to the positions of the plurality of device-electrode pairs in a one-to one manner, so that the different regions of the smoking material 112 are heated separately. The magnetic recording medium 160 can also include a plurality of sub-recording-mediums 160' disposed at different regions to store the information of the different regions of the smoking material 112. The aerosol-generating device 200 can also include a plurality of sub-magnetic-heads 260' corresponding to the plurality of sub-recording-mediums 160', so as to respectively read the information of the different regions of the smoking material 112. In an embodiment, the thermal insulating layer 140 extends along the radial direction and divides the smoking material 112 into a plurality of regions arranged along the axial direction of the aerosol-generating article 100. In another embodiment, the thermal insulating layer 140 extends along the axial direction and divides the smoking material 112 into a plurality of regions arranged along the radial direction of the aerosol-generating article 100.

Referring to FIG. 11 and FIG. 13 to FIG. 15, in an embodiment, the first article-electrode 122 and the second article-electrode 124 extend along the axial direction of the aerosol-generating article 100. For example, the length directions of the first article-electrode 122 and the second article-electrode 124 are parallel to the axial direction of the aerosol-generating article 100, so that the tubular shaped electric heating member 120 is electrically conducted along the circumferential direction thereof. The locations of the first article-electrode 122 and the second article-electrode 124 correspond to the locations of the device-electrodes of the aerosol-generating device 200, such as the first device-electrode 222 and the second device-electrode 224, in a one-to-one manner. In an embodiment, the first article-electrode 122 and the second article-electrode 124 are spaced apart from each other and disposed on two ends of the tubular electric heating member 120 in the radial direction; and the first device-electrode 222 and the second device-electrode 224 are spaced apart from each other and disposed on two ends of the tubular sidewall 202 in the radial direction. The shapes of the first device-electrode 222 and the second device-electrode 224 can respectively correspond to the shapes of the first article-electrode 122 and the second article-electrode 124. For example, the length directions of the first device-electrode 222 and the second device-electrode 224 are parallel to the axial direction of the tubular sidewall 202, and the lengths of the first device-electrode 222 and the second device-electrode 224 are substantially the same as that of the article-electrodes.

In this embodiment, the magnetic recording medium 160 can be a strip-shaped structure extending along the axial direction of the aerosol-generating article 100. The magnetic head 260 can move along the axial direction of the aerosol-generating article 100 when reading information, preventing the magnetic head 260 from rotating and approaching the electrodes. During the user puffs on the aerosol-generating article 100, the temperature about the electrodes is relatively high, which may damage the magnetic head 260. The magnetic recording medium 160 can be disposed at a middle portion between the first article-electrode 122 and the second article-electrode 124 and spaced from the first article-electrode 122 and the second article-electrode 124.

It can be understood that the positions of the first article-electrode 122 and the second article-electrode 124 can be determined according to the material and structure of the electric heating member 120 and the electrical connection method thereof with a power supply unit 210.

The aerosol-generating device 200 can further include the power supply unit 210 for providing direct current, such as a battery or a socket configured to be connected to an external power source. The positive and negative electrodes of the power supply unit 210 are electrically and respectively connected to the first device-electrode 222 and the second device-electrode 224 through wires 240. The control unit 230 can be configured to control the voltage and/or current provided to the device-electrodes, such as the first device-electrode 222 and/or the second device-electrode 224, from the power supply unit 210, so as to be functionalized as a switch and/or a temperature regulator. The power supply unit 210 and the control unit 230 can be disposed in the housing.

The aerosol-generating article 100 can further include a filter 130 disposed at one end of the article body 110 in the axial direction and at the air outflow end. The other end of the article body 110 is the air inflow end.

It can be understood that the magnetic recording medium 160 is not limited to covering the smoking material 112, being covered by the smoking material 112, and/or being disposed in the smoking material 112, or being disposed on the inner surface or the outer surface of the carrying tube 114. In an embodiment, the magnetic recording medium 160 can be disposed in the filter 130 or on a surface of the filter 130.

In an embodiment, the housing defines an opening communicating with the accommodating cavity 204, so that the aerosol-generating article 100 can be inserted into the accommodating cavity 204 through the opening.

It can be understood that the above embodiments can be combined with each other, and the aerosol-generating article 100 can include the electric heating members 120 and/or the information storage units disclosed in two or more different embodiments at the same time.

The aerosol-generating article according to the embodiments of the present disclosure can be applied to electronic cigarettes and low-temperature heating cigarettes, and can also be applied to other devices that need to heat specific materials, including but not limited to electric heating hookahs, tobacco pipes, and medical marijuana heating devices.

The technical features of the above-mentioned embodiments can be combined arbitrarily. In order to make the description concise, not all possible combinations of the technical features are described in the embodiments. However, as long as there is no contradiction in the combination of these technical features, the combinations should be considered as in the scope of the present application.

The above-described embodiments are only several implementations of the present application, and the descriptions are relatively specific and detailed, but they should not be construed as limiting the scope of the present application. It should be understood by those of ordinary skill in the art, without departing from the concept of the present application, various modifications and improvements can be made and all fall within the protection scope of the present application. Therefore, the patent protection of the present application shall be defined by the appended claims.

What is claimed is:

1. An aerosol-generating article, comprising:
an article body comprising smoking materials capable of generating aerosol; and
a magnetic recording medium disposed on a surface of the article body and/or inside the article body, wherein the magnetic recording medium is an information storage unit storing readable information; wherein the magnetic recording medium covers the smoking material, is covered by the smoking material, and/or is disposed in the smoking material.

2. The aerosol-generating article of claim 1, wherein the magnetic recording medium is film-shaped; the film-shaped magnetic recording medium is further constructed into a tubular structure; and the smoking material is disposed inside the tubular structure or carried by a surface of the tubular structure.

3. The aerosol-generating article of claim 1, wherein the readable information is attenuated or disappears at a temperature greater than a preset temperature, or the magnetic recording medium is weakened in magnetic strength or demagnetizes at the temperature greater than the preset temperature; the preset temperature is in a range from 100° C. to 300° C.

4. An aerosol-generating system, comprising
the aerosol-generating article of claim 1 and an aerosol-generating device.

5. The aerosol-generating article of claim 1, wherein
the article body further comprises a carrying tube; the smoking material is disposed in the carrying tube; and
the magnetic recording medium is disposed in the smoking material and wrapped by the smoking material or disposed on an inner surface or an outer surface of the carrying tube.

6. The aerosol-generating article of claim 5, wherein
the magnetic recording medium is a magnetic recording material layer directly disposed on the inner surface or the outer surface of the carrying tube.

7. The aerosol-generating article of claim 5, wherein
the magnetic recording medium comprises a magnetic recording material layer and a substrate stacked with each other; and a surface of the substrate away from the magnetic recording material layer is attached to the inner surface or the outer surface of the carrying tube.

8. The aerosol-generating article of claim 5, wherein the carrying tube is also an electric heating member.

9. The aerosol-generating article of claim 8, further comprising
a first article-electrode and a second article-electrode spaced apart from each other;
the first article-electrode and the second article-electrode are respectively disposed at two ends of the electric heating member in an axial direction and electrically connected to the electric heating member.

10. The aerosol-generating article of claim 9, wherein
the magnetic recording medium is a tubular structure and coaxially arranged with the electric heating member;
the magnetic recording medium is disposed between the first article-electrode and the second article-electrode and spaced apart from the first article-electrode and the second article-electrode.

11. The aerosol-generating article of claim 8, further comprising
a first article-electrode and a second article-electrode spaced apart from each other, the first article-electrode and the second article-electrode are respectively strip-shaped structures extending along an axial direction of the electric heating member.

12. The aerosol-generating article of claim 11, wherein
the magnetic recording medium is a strip-shaped structure extending along the axial direction of the electric heating member;
the magnetic recording medium is disposed between the first article-electrode and the second article-electrode and spaced apart from the first article-electrode and the second article-electrode.

13. The aerosol-generating article of claim 1, wherein
the magnetic recording medium is film-shaped, the film-shaped magnetic recording medium is constructed into a tubular structure, and the magnetic recording medium is also an electric heating member;
the magnetic recording medium comprises a material with both electric heating effect and magnetic property, or a composite of an electric heating material and a magnetic material.

14. An aerosol-generating device, configured to provide electrical energy or thermal energy to the aerosol-generating article of claim 1, wherein
the aerosol-generating device is provided with an accommodating cavity configured to accommodate the aerosol-generating article;

the aerosol-generating device comprises an information read unit; and the information read unit comprises a magnetic head disposed in the accommodating cavity and configured to read information.

15. The aerosol-generating device of claim 14, wherein the magnetic head is a plurality of magnetic heads; the plurality of magnetic heads are arranged along a circumferential direction or an axial direction of the accommodating cavity.

16. The aerosol-generating device of claim 14, further comprising:

a power supply unit;

a drive unit; and two device-electrodes, wherein the power supply unit is configured to supply electric power to an electric heating member of the aerosol-generating article; the power supply unit is electrically connected to the two device-electrodes; the two device-electrodes are disposed in the accommodating cavity; and the drive unit is configured to drive the magnetic head and/or the aerosol-generating article to move relative to each other.

17. The aerosol-generating device of claim 16, wherein the drive unit comprises a magnetic head drive unit, an aerosol-generating article drive unit, or a combination thereof, the magnetic head drive unit is connected to the magnetic head, and the magnetic head drive unit is configured to drive the magnetic head to rotate along a circumferential direction of the accommodating cavity or to move along an axial direction of the accommodating cavity;

the aerosol-generating article drive unit is connected to the aerosol-generating article, and the aerosol-generating article drive unit is configured to drive the aerosol-generating article to rotate along a circumferential direction of the accommodating cavity or to move along an axial direction of the accommodating cavity.

18. The aerosol-generating article of claim 13, wherein the magnetic recording medium is also a carrying tube, and the smoking material is filled in the tubular structure.

19. The aerosol-generating article of claim 18, wherein the carrying tube is also an electric heating member, the aerosol-generating article further comprises a first article-electrode and a second article-electrode spaced apart from each other, the first article-electrode and the second article-electrode are respectively disposed at two ends of the electric heating member in the axial direction and electrically connected to the electric heating member; the first article-electrode and the second article-electrode respectively faces to a first device-electrode and a second device-electrode of an aerosol-generating device.

20. An aerosol-generating article, comprising:

an article body comprising a smoking material capable of generating aerosol; and a magnetic recording medium covers the smoking material, is covered by the smoking material, and/or is disposed in the smoking material;

wherein the magnetic recording medium is an information storage unit storing readable information.

* * * * *